(12) United States Patent
Daly et al.

(10) Patent No.: US 8,679,074 B2
(45) Date of Patent: *Mar. 25, 2014

(54) PRESSURE RESPONSIVE SLIT VALVE ASSEMBLY FOR A PLURALITY OF FLUIDS AND USES THEREOF

(75) Inventors: Katie Daly, Boston, MA (US); Kristian DiMatteo, Waltham, MA (US)

(73) Assignee: AngioDynamics, Inc., Latham, NY (US)

( * ) Notice: Subject to any disclaimer, the term of this patent is extended or adjusted under 35 U.S.C. 154(b) by 110 days.

This patent is subject to a terminal disclaimer.

(21) Appl. No.: 13/165,286

(22) Filed: Jun. 21, 2011

(65) Prior Publication Data

US 2011/0313367 A1  Dec. 22, 2011

Related U.S. Application Data

(63) Continuation of application No. 10/390,854, filed on Mar. 18, 2003, now Pat. No. 7,988,679.

(51) Int. Cl.
*A61M 5/00* (2006.01)
*A61M 25/18* (2006.01)

(52) U.S. Cl.
USPC .......................................... 604/247; 604/537

(58) Field of Classification Search
USPC ............... 604/245–247, 256–257, 167.04, 604/167.03, 533–539, 278, 284
See application file for complete search history.

(56) References Cited

U.S. PATENT DOCUMENTS

| | | |
|---|---|---|
| 2,446,571 A | 3/1944 | Browne |
| 2,720,881 A | 10/1955 | Weaver et al. |
| 2,755,060 A | 7/1956 | Twyman |
| 3,113,586 A | 12/1963 | Edmark, Jr. |
| 3,159,175 A | 12/1964 | MacMillan |
| 3,159,176 A | 12/1964 | Russell et al. |
| 3,477,438 A | 11/1969 | Allen et al. |
| 3,514,438 A | 5/1970 | Nelsen et al. |
| 3,525,357 A | 8/1970 | Koreski |
| 3,621,557 A | 11/1971 | Cushman et al. |
| 3,669,323 A | 6/1972 | Harker et al. |
| 3,673,612 A | 7/1972 | Merrill et al. |
| 3,674,183 A | 7/1972 | Venable et al. |

(Continued)

FOREIGN PATENT DOCUMENTS

| DE | 20208420 | 10/2002 |
|---|---|---|
| EP | 0128625 | 12/1984 |

(Continued)

OTHER PUBLICATIONS

International Search Report and Written Opinion mailed Jun. 23, 2004 for International Application No. PCT/US2004/001606 (8 pages).

(Continued)

*Primary Examiner* — Kevin C Sirmons
*Assistant Examiner* — Andrew Gilbert
(74) *Attorney, Agent, or Firm* — Ryan D. Artis

(57) ABSTRACT

A pressure responsive slit valve assembly is designed to be used in a variety of configurations of medical devices to manage contemporaneous and pressure responsive fluid communications between such devices and a plurality of fluid sources. The pressure responsive slit valve assembly of the present invention includes a valve housing adapted to receive fluids from at least two sources and a pressure responsive slit valve means corresponding to each fluid sources.

6 Claims, 10 Drawing Sheets

(56) References Cited

U.S. PATENT DOCUMENTS

| | | | |
|---|---|---|---|
| 3,710,942 A | 1/1973 | Rosenberg | |
| 3,788,327 A | 1/1974 | Donowitz et al. | |
| 3,811,466 A | 5/1974 | Ohringer | |
| 3,941,149 A | 3/1976 | Mittleman | |
| 3,955,594 A | 5/1976 | Snow | |
| 4,072,146 A | 2/1978 | Howes | |
| 4,142,525 A | 3/1979 | Binard et al. | |
| 4,143,853 A | 3/1979 | Abramson | |
| 4,244,379 A | 1/1981 | Smith | |
| 4,387,879 A | 6/1983 | Tauschinski | |
| 4,405,316 A | 9/1983 | Mittleman | |
| 4,417,888 A * | 11/1983 | Cosentino et al. | 604/175 |
| 4,434,810 A | 3/1984 | Atkinson | |
| 4,447,237 A * | 5/1984 | Frisch et al. | 604/175 |
| 4,468,224 A | 8/1984 | Enzmann et al. | |
| 4,502,502 A | 3/1985 | Krug | |
| 4,524,805 A | 6/1985 | Hoffman | |
| 4,543,087 A | 9/1985 | Sommercorn et al. | |
| 4,552,553 A | 11/1985 | Schulte et al. | |
| 4,610,665 A | 9/1986 | Matsumoto et al. | |
| 4,616,768 A | 10/1986 | Flier | |
| 4,646,945 A | 3/1987 | Steiner et al. | |
| 4,673,393 A | 6/1987 | Suzuki et al. | |
| 4,681,572 A | 7/1987 | Tokarz et al. | |
| 4,692,146 A | 9/1987 | Hilger | |
| 4,722,725 A | 2/1988 | Sawyer et al. | |
| 4,790,832 A * | 12/1988 | Lopez | 604/523 |
| 4,798,594 A | 1/1989 | Hillstead | |
| 4,801,297 A | 1/1989 | Mueller | |
| 4,908,028 A | 3/1990 | Colon et al. | |
| 4,944,726 A | 7/1990 | Hilal et al. | |
| 4,946,448 A | 8/1990 | Richmond | |
| 4,960,412 A | 10/1990 | Fink | |
| 5,000,745 A | 3/1991 | Guest et al. | |
| 5,009,391 A | 4/1991 | Steigerwald | |
| 5,030,210 A | 7/1991 | Alchas et al. | |
| 5,084,015 A | 1/1992 | Moriuchi | |
| 5,098,405 A | 3/1992 | Peterson et al. | |
| 5,125,893 A | 6/1992 | Dryden | |
| 5,147,332 A | 9/1992 | Moorehead | |
| 5,149,327 A | 9/1992 | Oshiyama | |
| 5,167,638 A | 12/1992 | Felix et al. | |
| 5,169,393 A | 12/1992 | Moorehead et al. | |
| 5,176,652 A | 1/1993 | Littrell | |
| 5,176,662 A | 1/1993 | Bartholomew et al. | |
| 5,201,722 A | 4/1993 | Moorehead et al. | |
| 5,205,834 A | 4/1993 | Moorehead et al. | |
| 5,249,598 A | 10/1993 | Schmidt | |
| 5,254,086 A | 10/1993 | Palmer et al. | |
| 5,324,274 A | 6/1994 | Martin | |
| 5,330,424 A * | 7/1994 | Palmer et al. | 604/28 |
| 5,336,203 A | 8/1994 | Goldhardt et al. | |
| 5,360,407 A | 11/1994 | Leonard et al. | |
| 5,370,624 A | 12/1994 | Edwards et al. | |
| 5,395,352 A | 3/1995 | Penny | |
| 5,396,925 A | 3/1995 | Poli | |
| 5,399,168 A | 3/1995 | Wadsworth, Jr. et al. | |
| 5,401,255 A | 3/1995 | Sutherland et al. | |
| D357,735 S | 4/1995 | McPhee | |
| 5,405,340 A | 4/1995 | Fageol et al. | |
| 5,411,491 A | 5/1995 | Goldhardt et al. | |
| 5,453,097 A * | 9/1995 | Paradis | 604/247 |
| 5,454,784 A | 10/1995 | Atkinson et al. | |
| 5,469,805 A | 11/1995 | Gibbs et al. | |
| 5,470,305 A | 11/1995 | Arnett et al. | |
| 5,484,420 A | 1/1996 | Russo | |
| 5,542,923 A | 8/1996 | Ensminger et al. | |
| 5,545,150 A | 8/1996 | Danks et al. | |
| 5,554,136 A | 9/1996 | Luther | |
| 5,562,618 A | 10/1996 | Cai et al. | |
| 5,571,093 A * | 11/1996 | Cruz et al. | 604/270 |
| 5,575,769 A | 11/1996 | Vaillancourt et al. | |
| 5,624,395 A | 4/1997 | Mikhail et al. | |
| 5,637,099 A | 6/1997 | Durdin et al. | |
| 5,667,500 A | 9/1997 | Palmer et al. | |
| 5,707,357 A | 1/1998 | Mikhail et al. | |
| 5,743,873 A | 4/1998 | Cai et al. | |
| 5,743,884 A | 4/1998 | Hasson et al. | |
| 5,743,894 A | 4/1998 | Swisher | |
| 5,752,938 A | 5/1998 | Flatland et al. | |
| 5,792,402 A * | 8/1998 | Rivers et al. | 264/103 |
| 5,803,078 A | 9/1998 | Brauner | |
| 5,807,349 A | 9/1998 | Person et al. | |
| 5,810,789 A | 9/1998 | Powers et al. | |
| 5,843,044 A | 12/1998 | Moorehead | |
| 5,853,397 A | 12/1998 | Shemesh et al. | |
| 5,865,308 A | 2/1999 | Qin et al. | |
| 5,944,698 A | 8/1999 | Fischer et al. | |
| 5,984,902 A | 11/1999 | Moorehead | |
| 5,989,233 A | 11/1999 | Yoon | |
| 6,033,393 A | 3/2000 | Balbierz et al. | |
| 6,045,734 A | 4/2000 | Luther et al. | |
| 6,050,934 A | 4/2000 | Mikhail et al. | |
| 6,056,717 A | 5/2000 | Finch et al. | |
| 6,062,244 A * | 5/2000 | Arkans | 137/1 |
| 6,092,551 A | 7/2000 | Bennett | |
| 6,099,505 A | 8/2000 | Ryan et al. | |
| 6,120,483 A | 9/2000 | Davey et al. | |
| 6,152,909 A | 11/2000 | Bagaoisan et al. | |
| 6,210,366 B1 | 4/2001 | Sanfilippo | |
| 6,227,200 B1 | 5/2001 | Crump et al. | |
| 6,270,489 B1 | 8/2001 | Wise et al. | |
| 6,306,124 B1 | 10/2001 | Jones et al. | |
| 6,364,861 B1 | 4/2002 | Feith et al. | |
| 6,364,867 B2 | 4/2002 | Wise et al. | |
| 6,375,637 B1 | 4/2002 | Campbell et al. | |
| 6,436,077 B1 | 8/2002 | Davey et al. | |
| 6,442,415 B1 | 8/2002 | Bis et al. | |
| 6,446,671 B2 | 9/2002 | Armenia et al. | |
| 6,508,791 B1 | 1/2003 | Guerrero | |
| 6,551,270 B1 * | 4/2003 | Bimbo et al. | 604/93.01 |
| 6,610,031 B1 | 8/2003 | Chin | |
| 6,726,063 B2 | 4/2004 | Stull et al. | |
| 6,786,884 B1 | 9/2004 | DeCant et al. | |
| 6,874,999 B2 | 4/2005 | Dai et al. | |
| 6,953,450 B2 | 10/2005 | Baldwin et al. | |
| 6,994,314 B2 | 2/2006 | Garnier et al. | |
| 7,081,106 B1 | 7/2006 | Guo et al. | |
| 7,163,531 B2 * | 1/2007 | Seese et al. | 604/533 |
| 7,252,652 B2 | 8/2007 | Moorehead et al. | |
| 7,291,133 B1 | 11/2007 | Kindler et al. | |
| 7,316,655 B2 | 1/2008 | Garibotto et al. | |
| 7,435,236 B2 | 10/2008 | Weaver et al. | |
| 7,601,141 B2 | 10/2009 | Dikeman et al. | |
| 7,637,893 B2 | 12/2009 | Christensen et al. | |
| 7,758,541 B2 | 7/2010 | Wallace et al. | |
| 7,988,679 B2 * | 8/2011 | Daly et al. | 604/247 |
| 8,034,035 B2 * | 10/2011 | Weaver et al. | 604/247 |
| 2001/0023333 A1 | 9/2001 | Wise et al. | |
| 2001/0037079 A1 | 11/2001 | Burbank et al. | |
| 2002/0010425 A1 | 1/2002 | Guo et al. | |
| 2002/0016584 A1 | 2/2002 | Wise et al. | |
| 2002/0121530 A1 * | 9/2002 | Socier | 222/494 |
| 2002/0165492 A1 | 11/2002 | Davey et al. | |
| 2002/0193752 A1 | 12/2002 | Lynn | |
| 2003/0122095 A1 | 7/2003 | Wilson et al. | |
| 2004/0034324 A1 | 2/2004 | Seese et al. | |
| 2004/0064128 A1 | 4/2004 | Raijman et al. | |
| 2004/0102738 A1 | 5/2004 | Dikeman et al. | |
| 2004/0108479 A1 | 6/2004 | Garnier et al. | |
| 2004/0186444 A1 | 9/2004 | Daly et al. | |
| 2004/0193119 A1 | 9/2004 | Canaud et al. | |
| 2004/0210194 A1 | 10/2004 | Bonnette et al. | |
| 2004/0267185 A1 | 12/2004 | Weaver et al. | |
| 2005/0010176 A1 | 1/2005 | Dikeman et al. | |
| 2005/0027261 A1 | 2/2005 | Weaver et al. | |
| 2005/0043703 A1 | 2/2005 | Nordgren | |
| 2005/0049555 A1 | 3/2005 | Moorehead et al. | |
| 2005/0149116 A1 | 7/2005 | Edwards et al. | |
| 2005/0171490 A1 | 8/2005 | Weaver et al. | |
| 2005/0171510 A1 | 8/2005 | DiCarlo et al. | |
| 2005/0283122 A1 | 12/2005 | Nordgren | |
| 2006/0129092 A1 | 6/2006 | Hanlon et al. | |
| 2006/0135949 A1 | 6/2006 | Rome et al. | |

(56) References Cited

U.S. PATENT DOCUMENTS

| | | | |
|---|---|---|---|
| 2006/0149211 | A1 | 7/2006 | Simpson et al. |
| 2007/0161940 | A1 | 7/2007 | Blanchard et al. |
| 2007/0161970 | A1 | 7/2007 | Spohn et al. |
| 2007/0276313 | A1 | 11/2007 | Moorehead et al. |
| 2008/0108956 | A1 | 5/2008 | Lynn et al. |
| 2009/0292252 | A1 | 11/2009 | Lareau et al. |

FOREIGN PATENT DOCUMENTS

| | | |
|---|---|---|
| EP | 0337617 | 10/1989 |
| EP | 0930082 | 7/1999 |
| EP | 1016431 | 7/2000 |
| FR | 2508008 | 12/1982 |
| FR | 2718969 | 10/1995 |
| GB | 966137 | 8/1964 |
| GB | 2102398 | 2/1983 |
| JP | 59133877 | 8/1984 |
| JP | 63255057 | 10/1988 |
| JP | 9038197 | 2/1997 |
| WO | WO-89/02764 | 4/1989 |
| WO | WO-91/12838 | 9/1991 |
| WO | WO-92/06732 | 4/1992 |
| WO | WO-95/16480 | 6/1995 |
| WO | WO-96/17190 | 6/1996 |
| WO | WO-96/23158 | 8/1996 |
| WO | WO-96/41649 | 12/1996 |
| WO | WO-97/23255 | 7/1997 |
| WO | WO-97/26931 | 7/1997 |
| WO | WO-98/22178 | 5/1998 |
| WO | WO-99/42166 | 8/1999 |
| WO | 0006230 | 2/2000 |
| WO | WO-00/44419 | 8/2000 |
| WO | WO-01/74434 | 10/2001 |
| WO | WO-03/084832 | 10/2003 |
| WO | WO-2005/023355 | 3/2005 |
| WO | WO-2008/089985 | 7/2008 |

OTHER PUBLICATIONS

International Preliminary Report on Patentability mailed Sep. 23, 2005 for International Application No. PCT/US2004/001606 (6 pages).

Asch, "Venous access: options, approaches and issues," Can Assoc. Radiol J., vol. 52, No. 3 pp. 153-164 (2001).

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

\* cited by examiner

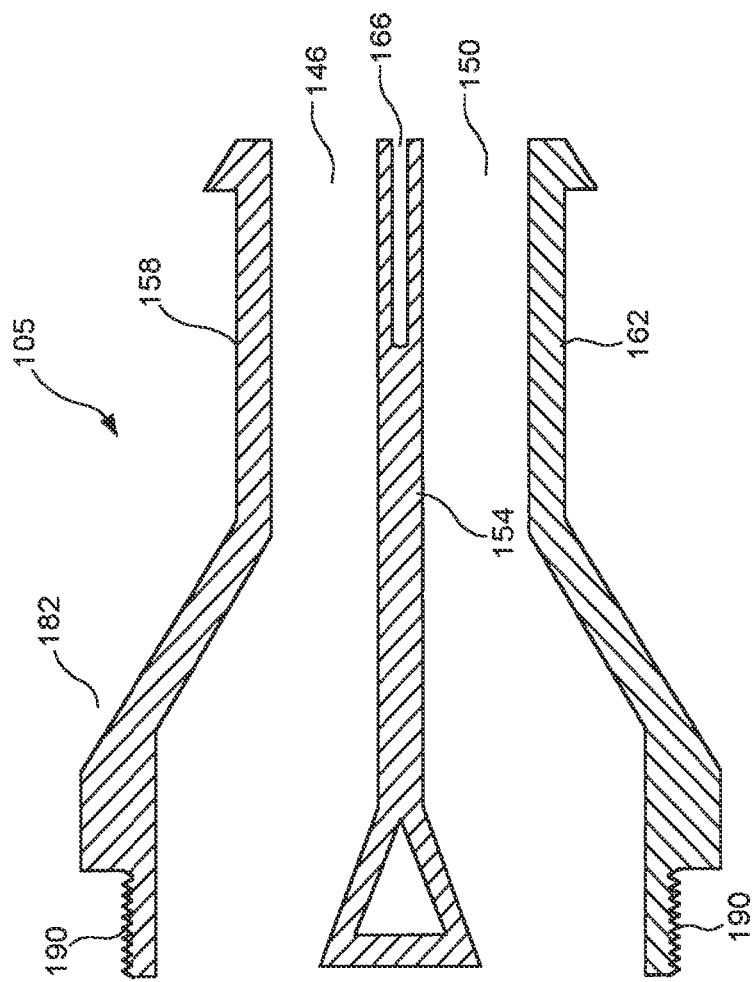
FIG. 1B
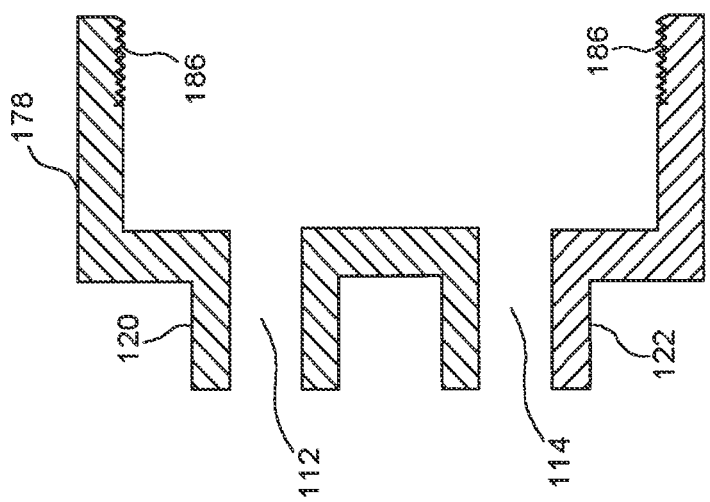

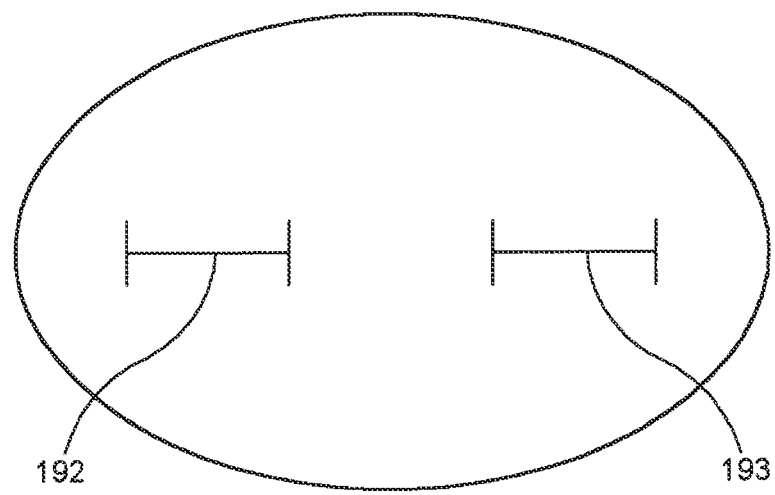
F I G. 6
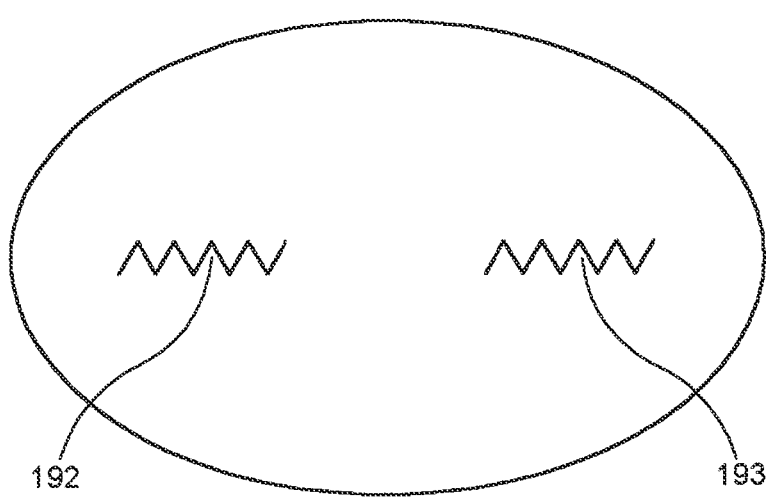
F I G. 7

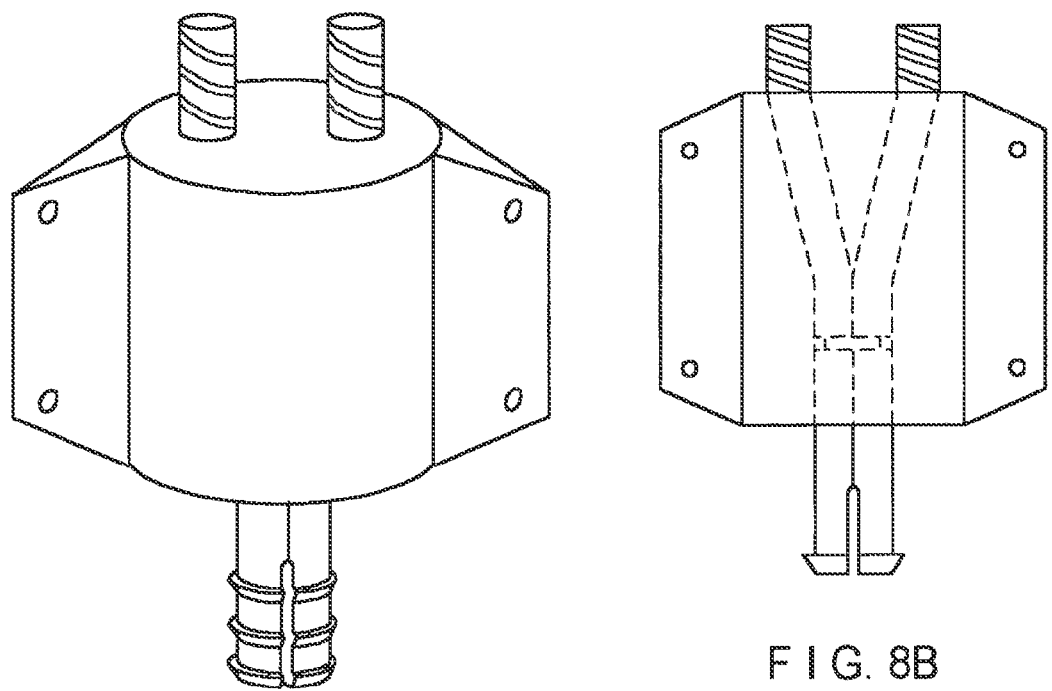
FIG. 8A
FIG. 8B
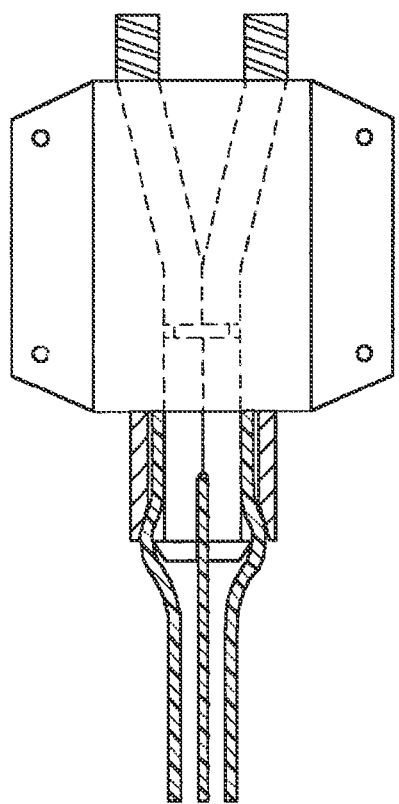
FIG. 8C

PRESSURE RESPONSIVE SLIT VALVE ASSEMBLY FOR A PLURALITY OF FLUIDS AND USES THEREOF

CROSS-REFERENCE TO PRIOR APPLICATIONS

This application is a continuation of, and claims priority to, U.S. application Ser. No. 10/390,854, filed on Mar. 18, 2003, now U.S. Pat. No 7,988,679.

TECHNICAL FIELD

This invention relates to medical devices. More particularly, this invention relates to medical devices accommodating a plurality of medical fluid sources including body fluids.

BACKGROUND INFORMATION

Dual-lumen or multi-lumen medical devices are typically employed to deliver different drugs, blood products, nutritional fluids, or other fluids into the vascular system, peritoneal or epidural space, or other locations within a patient, body. Accordingly, it is medically desirable to manage contemporaneous fluid communications between such medical devices and a plurality of fluid sources. Furthermore, it has also been long recognized to be medically desirable to control fluid flow in a pressure responsive fashion to prevent undesired fluid flows that usually cause leakage and blood clotting. Pressure Activated Safety Valve Technology available under the trademark PASV® Valve Technology from Boston Scientific Corporation, Natick, Mass., has been employed in medical devices to control fluid flow. A single lumen pressure responsive slit valve housing is described in U.S. Pat. Nos. 5,169,393, 5,205,834, and 5,843,044, the entire contents of each of which are incorporated herein by reference. Such a single lumen design, however, has a limited ability to accommodate a dual lumen or multi-lumen medical device. For example, use of a single lumen valve housing in a dual lumen port requires clumsy intermediate connectors to accommodate fluid flow from spatially separated lumens into the side-by-side configuration necessitated by the dimensions of a multi-lumen catheter. This intermediate connector structure is cumbersome, subject to leakage and compromises the sterility of the fluids flowing therein. Naturally, this also complicates the process of manufacture and assembly, and increases its cost, as well as increases the chances of structural failure.

SUMMARY OF THE INVENTION

It is an object of the present invention to provide a pressure responsive slit valve assembly that can effectively accommodate management of a plurality of fluids in a variety of medical devices. It is also an object of the present invention to provide a pressure responsive slit valve assembly that can be an interchangeable component of a medical device. In one preferred embodiment, a pressure responsive slit valve assembly of the present invention generally includes a valve housing that is adapted to receive fluids from at least two fluid sources, and a pressure responsive slit valve means corresponding to each fluid source.

The valve housing defines two apertures, a first aperture for receiving a first fluid, and a second aperture for receiving a second fluid. The first and the second apertures are not in fluid communication with each other. Accordingly, the fluids entering the valve housing are maintained in an unmixed state. The valve housing further defines a flow means that includes a first conduit and a second conduit. The first conduit is situated longitudinally therethrough and is in fluid communication with the first aperture. Similarly, the second conduit is situated longitudinally therethrough and is in fluid communication with the second aperture. The first and the second conduits are not in fluid communication with each other so that the fluids are maintained in an unmixed state. In one embodiment, the valve housing can be made of a metal, preferably, titanium. In another embodiment, the valve housing can be made of plastic.

The slit valve means generally includes a first pressure responsive slit and a second pressure responsive slit. The first slit is disposed transversely between and in fluid communication with the first aperture and the first conduit. The first slit deforms in response to the pressure differential associated with the first fluid thereby to allow the first fluid to flow in a desired direction. The second slit is disposed transversely between and is in fluid communication with the second aperture and the second conduit. The second slit deforms in response to the pressure differential associated with the second fluid thereby to allow the second fluid to flow in a desired direction.

In another embodiment, the pressure responsive slit valve assembly of the present invention includes a valve housing that is further adapted to receive at least one additional fluid from an additional source. Accordingly, the further adapted valve housing includes at least one additional corresponding aperture and at least one additional corresponding conduit, and the slit valve means further includes at least one additional corresponding pressure responsive slit.

In yet another embodiment, the pressure responsive slit valve assembly of the present invention includes a valve housing that further defines a first chamber for the first fluid, and a second chamber for the second fluid. The first and the second chambers are not in fluid communication with each other so that the fluids are maintained in an unmixed state.

In one preferred embodiment, the pressure responsive slit valve assembly of the present invention further includes a first connection port for receiving the first fluid and a second connection port for receiving the second fluid. The first connection port is in communication with the first aperture, and the second connection port is in communication with the second aperture. The first and second connection ports do not communicate with each other such that the first and second fluids are maintained in an unmixed state. In other embodiments, the first and second connection ports may further embody alignment means on the exterior surface thereof for aligning the pressure responsive slit valve assembly with a medical device. The alignment means includes, but are not limited to, grooves, barbs, threads, and other suitable physical features on the exterior surfaces of the connection ports.

In another preferred embodiment, the pressure responsive slit valve means of the present invention further comprises a first extrusion stem defining the first conduit, and a second extrusion stem defining the second conduit. The first and second extrusion stems are typically configured to be receivable individually inside each corresponding lumen of a medical device. Embodiments of the extrusion stems may further include the following features: For example, in one embodiment, the extrusion stems are substantially contiguous proximal to the valve housing. In yet another embodiment, the extrusion stems may further embody securement means to ensure secure attachment of a medical device to the extrusion stems. The securement means includes, but are not limited to, barbs, threads and other suitable physical features on the exterior surfaces of the extrusion stems. In some embodiments, the securement means may further include a locking sleeve engageable to the extrusion stems.

In yet another preferred embodiment, the slit valve means includes one elastomeric diaphragm that embodies the first and the second pressure responsive slits. In an alternative embodiment, the slit valve means includes a first diaphragm that embodies the first pressure responsive slit, and a second diaphragm that embodies the second pressure responsive slit. In either of these embodiments, the elastomeric diaphragm may be disc-shaped. Alternatively, the elastomeric diaphragm may be rectangular-shaped. In other embodiments, the slit valve means may further include a diaphragm securement means adjacent the periphery of the slit valve means.

It is another object of the present invention to provide medical devices that comprise a pressure responsive slit valve assembly. The embodiments of medical devices include, but are not limited to, dual-lumen or multi-lumen implantable ports, dual-lumen or multi-lumen Peripherally Inserted Central Catheters (PICC), dual-lumen or multi-lumen tunneled central venous catheters, and dual-lumen or multi-lumen dialysis catheters, to name but a few. The present invention is suitable for use in any medical device in which a plurality of fluids is employed.

It is yet another object of the present invention to provide a kit for adapting a medical device to manage a plurality of fluids. The kit typically includes an assembly that is adapted for connecting to a medical device to receive fluids from at least two fluid sources. The assembly comprises pressure responsive means corresponding to each fluid sources, and further comprises securement means for securely adapting the medical device.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1B is a schematic view of a female part valve housing and a male part valve housing of an exemplary embodiment of a pressure responsive slit valve assembly of the present invention.

FIG. 6 is a cross-sectional view of an exemplary embodiment of pressure responsive slits.

FIG. 7 is a cross-sectional view of an alternative embodiment of pressure responsive slits.

FIG. 8A is a perspective view of an exemplary embodiment of a pressure responsive slit valve assembly of the present invention adapted to a PICC catheter.

FIG. 8B is a schematic view of an exemplary embodiment of a pressure responsive slit valve assembly of the present invention adapted to a PICC catheter.

FIG. 8C is a schematic view of an exemplary embodiment of a pressure responsive slit valve assembly of the present invention with a dual-lumen PICC catheter attached thereon.

DETAILED DESCRIPTION

The present invention provides a pressure responsive slit valve assembly (also referred to herein as "valve assembly") that can be used in a variety of configurations of medical devices to manage contemporaneous and pressure responsive fluid communications between such devices and a plurality of fluid sources. The medical devices suitable for use with the pressure responsive slit valve assembly of the present invention include, but are not limited to, dual-lumen or multi-lumen implantable ports, dual-lumen or multi-lumen Peripherally Inserted Central Catheters (PICC), dual-lumen or multi-lumen tunneled central venous catheters, dual-lumen or multi-lumen dialysis catheters, to name but a few. It is further contemplated that a pressure responsive slit valve assembly of the present invention can be interchangeably and removably connected to a medical device. Alternatively, the connection between a pressure responsive slit valve assembly of the present invention and a medical device can be permanent and fixed. Whether used as an interchangeable component adapted for use with a variety of medical devices, or whether used as an integral component of a medical device adapted for use during its manufacture, the pressure responsive slit valve assembly of the present invention permits contemporaneous management of a plurality of fluids without mixing of said fluids.

Figure 1A:
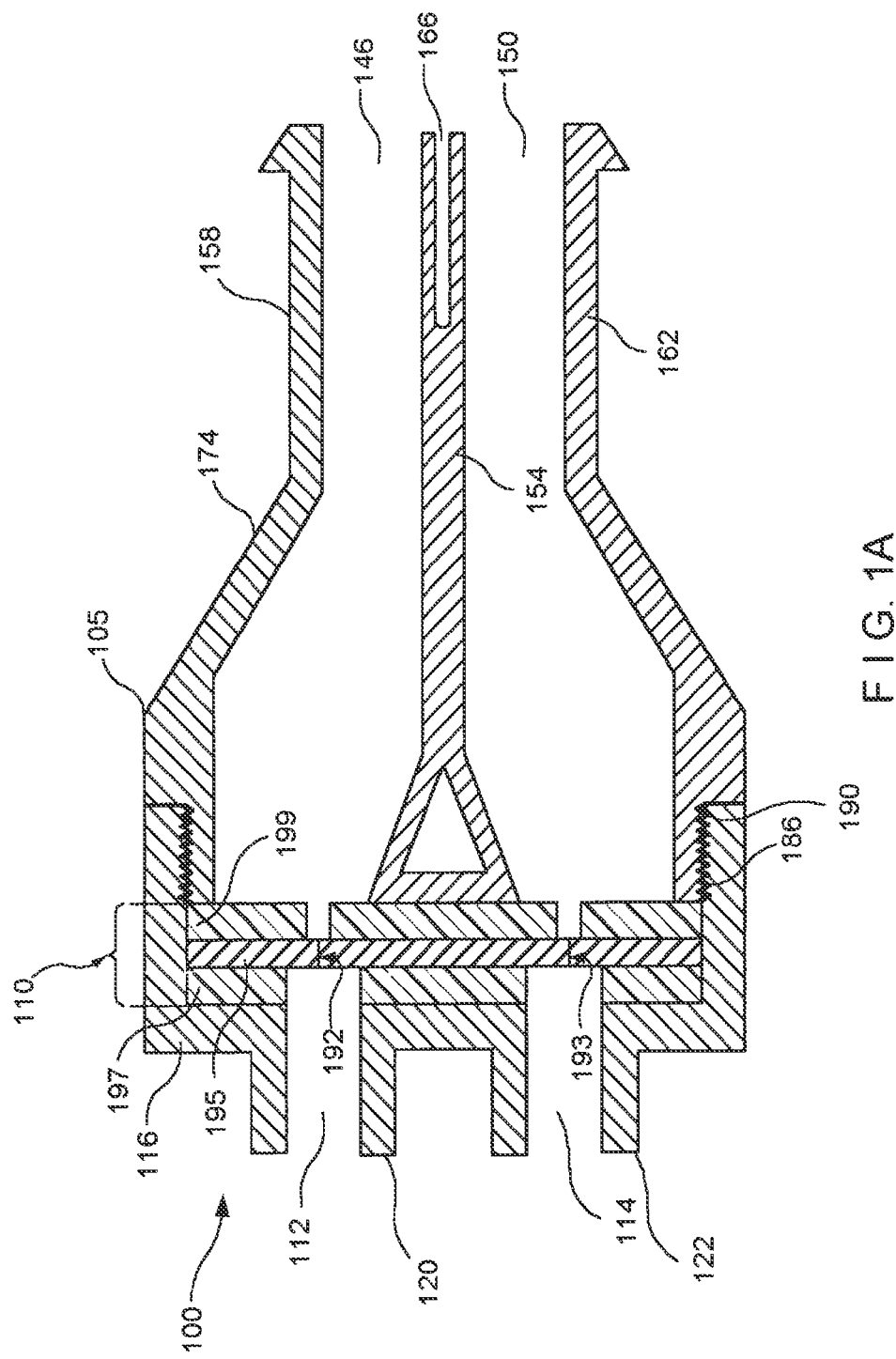
FIG. 1A is a schematic view of an exemplary embodiment of a pressure responsive slit valve assembly of the present invention.

Referring to FIG. 1A, a schematic view of an exemplary embodiment of a pressure responsive slit valve assembly 100 of the present invention is shown. The valve assembly 100, as illustrated in FIG. 1A, generally includes a valve housing 105, and a slit valve means 110.

The valve housing 105 is adapted to receive fluids from at least two sources. Accordingly, the valve housing 105 is preferably made from rigid, shape-retaining materials including, but not limited to, metals, preferably titanium, or stainless steel, and ceramics, polymers or plastics such as, for example, polysulphone, polycarbonate, polyethylene, plastics sold under the trademark GRILAMID® from EMS-Chemie AG Corporation, Reichenauerstrasse, Switzerland, or synthetic resinous materials sold under the trademark ULTEM® from General Electric Company Corporation, Pittsfield, Mass. Suitable shapes for the valve housing 105 include but are not limited to, cylindrical shapes, cubic shapes, tubular shapes, and other shapes.

Figure 3:
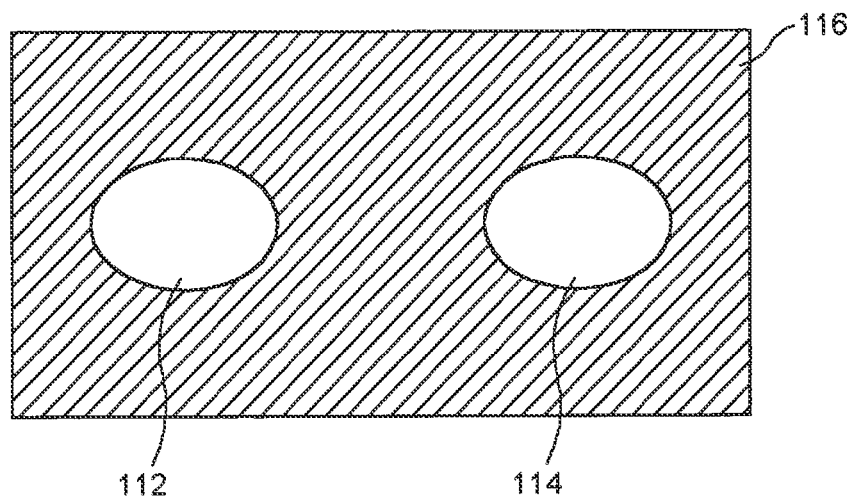
FIG. 3 is a cross-sectional view of an exemplary embodiment of first and second apertures defined by the valve housing.

The valve housing 105 defines a first aperture 112 for receiving a first fluid, and a second aperture 114 for receiving a second fluid. It is contemplated that the first and second apertures 112 and 114 are not in fluid communication with each other such that the fluids are maintained in an unmixed state. The configuration of the first and second apertures generally accommodates the fluid sources in a medical device. In one embodiment, the first and second apertures 112 and 114 are both located on the vertical wall 116 of the valve housing 105. Referring to FIG. 3, a cross-sectional view of an exemplary embodiment of the first and second apertures 112 and 114 is shown. In this embodiment, the first and second apertures 112 and 114 are both oval-shaped. They can also be circular-shaped or any other suitable shapes, including shapes suitable for high flow designs. In other embodiments, the first and second apertures 112 and 114 may be located on the other parts of the valve housing 105 to accommodate the design of a medical device. For example, the first and second apertures 112 and 114 may be located on the top of the valve housing 105.

In a preferred embodiment, the valve assembly 100 can further comprise a first connection port 120 and a second connection port 122 to facilitate connection and fluid communication between the valve assembly 100 and a medical device. For example, connection ports 120 and 122 can be employed to mediate direct or indirect connection between the valve assembly 100 and a dual-lumen implantable port. As depicted in FIG. 1A, the first and second connection ports 120 and 122 that join the valve housing 105 at the vertical wall 116 are adapted to receive first and second fluids, respectively, from two spatially separated fluid cavities in a dual-lumen implantable port. In other embodiments, the first and second connection ports 120 and 122 may join the other parts of the valve housing 105 to accommodate the design of a medical device. For example, the connection ports 120 and 122 may join the top of the valve housing 105. In each instance, the first connection port 120 is in fluid communication with the first aperture 112, and the second connection port is in fluid communication with the second aperture 114. It is contemplated that the first and the second connection ports 120 and 122 do not communicate with each other such that the fluids are maintained in an unmixed state.

The connection ports 120 and 122 are preferably made of the same material as the valve housing 105, but may be made of any suitable material that is sufficiently rigid and is compatible with the material of the valve housing 105. It is contemplated that the connection ports 120 and 122 may be an integral part of the valve housing 105. It is also contemplated that the connection ports 120 and 122 may be permanently fixed to the valve housing 105 by adhesives or overmolding methods. In a preferred embodiment, the connection ports 120 and 122 are contemplated to be male connectors in nature, which can directly or indirectly fit into corresponding female fluid cavities in a medical device. The exterior shape of the connection ports 120 and 122 can be cylindrical, tubular, or other shapes. They may also be bent at a predetermined angle or curved to allow more smooth transition from the fluid cavities in a medical device to the valve housing 105. In addition, the connection ports 120 and 122 can further embody threads, barbs, grooves, or other physical features on the exterior surfaces to facilitate secure connections between the connection ports and the fluid cavities in a medical device.

Figure 4A:
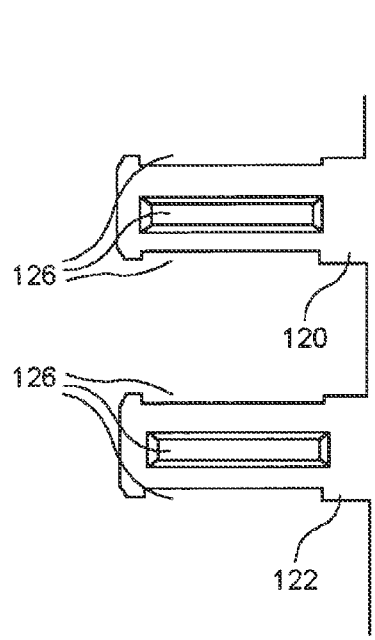
FIG. 4A is a schematic view of the exterior surfaces of the connection ports of an exemplary embodiment of the present invention.
Figure 4C:
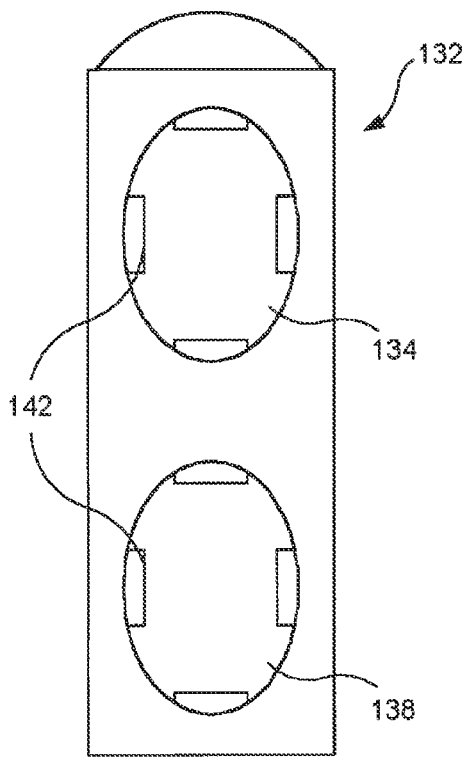
FIG. 4C is a schematic view of an alternative embodiment of a dual-lumen port.
Figure 4B:
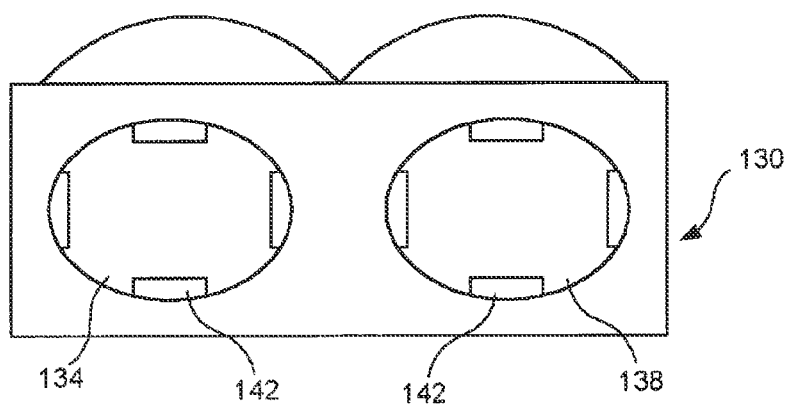
FIG. 4B is a schematic view of an exemplary embodiment of a dual-lumen port.

Referring to FIGS. 4A, 4B and 4C, exemplary embodiments of the exterior surfaces of connection ports 120 and 122 and the corresponding female fluid cavities in a dual-lumen port are shown. As illustrated in FIG. 4A, the connection ports 120 and 122 each embodies a plurality of grooves 126 on the exterior surfaces thereof. As illustrated in FIG. 4B, a dual lumen port 130 embodies two horizontally aligned separate fluid cavities 134 and 138. The fluid cavities 134 and 138 each embodies a plurality of barbs 142 extruding inwardly from the corresponding interior surfaces thereof. The number of barbs 142 on the interior surface of the fluid cavities 134 and 138 corresponds to the number of grooves 126 on the exterior surfaces of connection port 120 and 122. Furthermore, the shapes and dimensions of barbs 142 are designed to fit into corresponding grooves 126 on the exterior surfaces of the connection ports 120 and 122. An alternative embodiment of a dual-lumen port 132 is shown in FIG. 4C, where the two separate fluid cavities 134 and 138 are aligned vertically. As in FIG. 4B, the fluid cavities 134 and 138 each embodies a plurality of barbs 142 extruding inwardly from the corresponding interior surfaces thereof. In either embodiment, the male connection ports 120 and 122 as illustrated in FIG. 4A can press fit into the corresponding fluid cavities as illustrated in FIG. 4B or 4C. It is contemplated that the grooves 126 can cause the male connection ports 120 and 122 to align with the female fluid cavities 134 and 138 to allow a liquid tight connection between the valve assembly 100 and the dual-lumen port 130 or 132. It can be readily appreciated that the press-fit connection between the valve assembly 100 and the dual-lumen port 130 or 132 can be removable or interchangeable. The connection can be accomplished by physicians or nurses during a medical procedure. The connection can also be accomplished during the manufacture of the dual-lumen port. When permanent attachment is desired, a suitable sealing material or adhesive can be applied between the interior surfaces of the fluid cavities in the port and the corresponding exterior surfaces of the connection ports. Sonic welding, adhesive bonding, or other suitable means of permanently affixing the valve assembly 100 are contemplated. In yet another embodiment, the male connection ports without grooves on the exterior surface thereof are contemplated. For example, using a friction or press fit, the male connection ports can also be connected to the corresponding female fluid cavities in the port by friction forces. Other types of mechanical or non-mechanical forces are also contemplated.

The valve housing 105 further defines a flow means which typically includes a first conduit 146 for the first fluid and a second conduit 150 for the second fluid. The first and second conduits 146 and 150 are longitudinally therethrough in communication with the first and second apertures 112 and 114, respectively. It is contemplated that the first and second conduits 146 and 150 do not communicate with each other such that the first and second fluids are maintained in an unmixed state. As illustrated in FIG. 1A, inside the valve housing 105, the first and second fluids are separated by internal walls 154. The internal walls 154 are configured to avoid sharp ends and edges such that the flows of the fluids can be smoothly directed from the apertures 112 and 114 into the conduits 146 and 150, respectively.

In a preferred embodiment, the valve housing 105 further comprises a first extrusion stem 158 that defines the first conduit 146, and a second extrusion stem 162 that defines the second conduit 150. The first and second extrusion stems 158 and 162 are generally configured to be receivable individually into each of corresponding lumens in a desired medical device. For example, as illustrated in FIG. 1A, the first and second extrusion stems 158 and 162 are configured to be receivable individually inside each of corresponding lumens of a dual-lumen catheter. In this configuration, the two extrusion stems 158 and 162 are substantially contiguous proximal to the valve housing 105, but are separated at the distal end defining a slot 166 between the two stems. The slot 166 defined between the two stems 158 and 162 should be wide enough to fit an inner wall of a dual-lumen catheter, therefore, allows each extrusion stems to be individually receivable into each of corresponding lumens of a dual-lumen catheter. The exterior structure of first and second extrusion stems 158 and 162 of this exemplary embodiment is depicted in more detail in FIG. 5.

Figure 5:
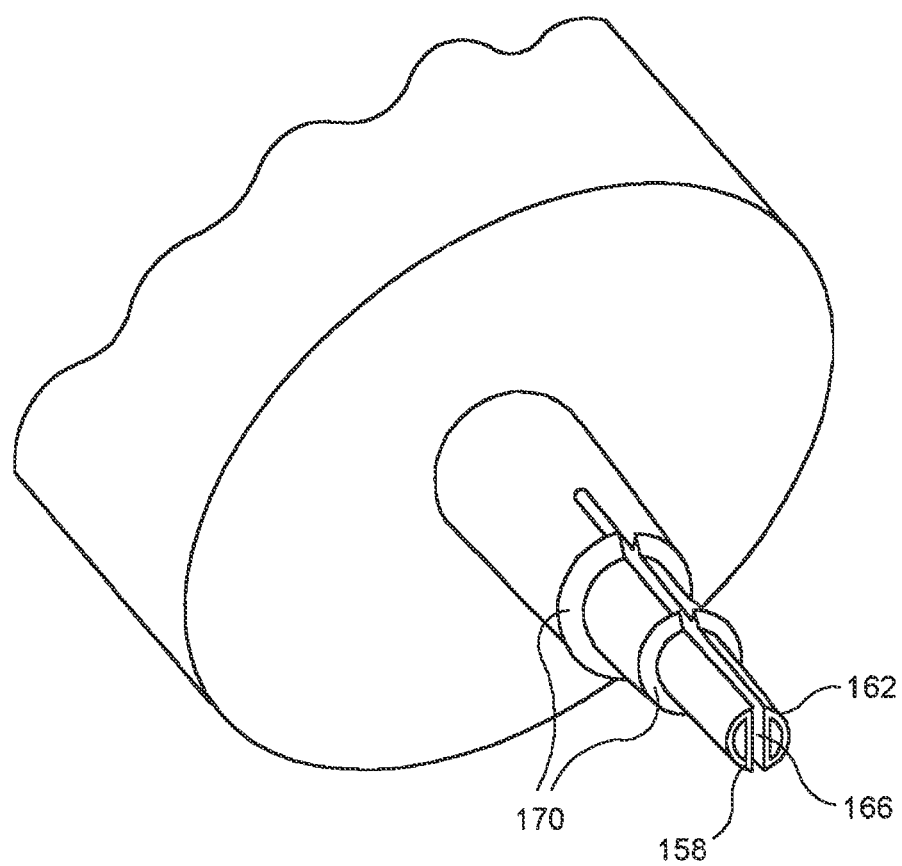
FIG. 5 is a perspective view of the exterior structure of the extrusion stems of an exemplary embodiment of the present invention.

As illustrated in FIG. 5, extrusion stems 158 and 162 are configured for use in a dual-lumen catheter having lumens that are generally D-shaped. However, catheters having a plurality of lumens of other configurations can be used with the present invention and, accordingly, correspondingly shaped extrusion stems are within the scope of the present invention. For example, catheters having round lumens, smile lumens, non-concentric lumens, and other types of lumens are contemplated. In each instance, the number and shape of the stems are configured to correspond with the number and the shape of the lumens of the catheter to be slid over the stems.

In a preferred embodiment, the first and second extrusion stems 158 and 162 may further embody securement means to secure the attachment of a medical device to the extrusion stems. For example, the extrusion stems 158 and 162 may further embody one or more barbs 170 on the exterior surfaces thereof to ensure a secure fit between the extrusion stems and a dual lumen catheter. As illustrated in FIG. 5, the barbs 170 on the exterior surfaces of the extrusion stems 158 and 162 taper towards the distal end of the stems with decreasing circumferences. It is contemplated that this configuration of the barbs allows the catheters to be easily slid thereover, but generates enough tension to prevent inadvertent separation between the catheter and the stems. Other types of barb designs are also within the scope of the present invention. Suitable barb configurations include, but are not limited to, stepped barb configurations, preferably those with pure rectangular steps, and those with the rise at an angle. Furthermore, the valve assembly 100 of the present invention may further comprise a locking sleeve (not shown) that can slide over the catheter to further compress the catheter on the extrusion stems to secure the attachment. Suitable locking sleeves include, but are not limited to, a press-on lock, screw lock, and swivel lock.

As depicted in FIG. 1A, extrusion stems 158 and 162 integrally join the valve housing 105 at the wall 174. The wall 174 may be vertical such that the extrusion stems 158 and 162 join the wall 174 at 90° angle. Alternatively, the wall 174 may be tapered to accommodate the change from the larger configuration of the valve housing 105 to the generally smaller configuration of the extrusion stems 158 and 162. Accordingly, the extrusion stems 158 and 162 join the wall 174 at an angle larger than 90°. In addition, it is contemplated that the extrusion stems 158 and 162 may be permanently fixed to the housing 105 by adhesives or overmolding methods.

As shown in FIG. 1A, a longitudinal sectional view of the internal lumens of the valve assembly 100 is generally in a "Y" configuration to bring the two separated fluid flows into closely parallel extrusion conduits. It can be readily appreciated that other types of lumen configurations are also within the scope of the present invention. The internal lumens of a pressure responsive slit valve assembly is generally configured to correspond to and accommodate the shape of the valve housing, the location of the apertures and the design of the extrusion stems.

It can be readily appreciated by a person of skill in the art that the valve housing 105 can be manufactured and assembled in different ways to accommodate the desired configuration and the selected material of the valve housing. For example, in one embodiment, as shown in FIG. 1B, the valve housing 105 can be formed from a female part 178, and a male part 182. As depicted in FIG. 1B, the female part 178 can generally include the first and second apertures 112 and 114, and two connection ports 120 and 122. The male part 182 can generally include the first and second extrusion stems 158 and 162, and the internal walls 154. The male and female parts 178 and 182 are constructed such that one sealingly connects to the other. For example, the female part 178 can have a relatively larger annular wall with internal threads 186. The male part 182 can have a relatively smaller annular wall with external threads 190. Accordingly, as illustrated in FIG. 1A, the male part 182 can frictionally fit into the female part 178 such that the internal threads 186 and the external threads 190 can interact with each other to generate frictional forces. Instead of frictional forces, an adhesive can be used to secure a bond between the female part 178 and the male part 182. Alternatively, a female part 178 and a male part 182 can be thermally, chemically, mechanically or ionically bonded together.

As illustrated in FIG. 1A, the slit valve means 110 of the pressure responsive slit valve assembly 100 generally includes a first slit 192 and a second slit 193. The first slit 192 is disposed transversely between and in communication with the first conduit 146 and the first aperture 112. Accordingly, the first slit 192 is responsive to a pressure differential associated with the first fluid. In particular, the first slit 192 remains in a closed position until a pressure differential having a predetermined force exists across the first slit 192. Once the pressure differential crosses over this predetermined force threshold, the first slit 192 deforms, thereby allowing the first fluid to flow therethrough in a desired direction. Similarly, the second slit 193 is disposed transversely between and in communication with the second conduit 150 and the second aperture 114. Accordingly, the second slit is responsive to a pressure differential associated with the second fluid. In particular, the second slit 193 remains in a closed position until a pressure differential having a predetermined force exists across the second slit 193. Once the pressure differential crosses over this predetermined force threshold, the second slit 193 deforms, thereby allowing the second fluid to flow therethrough in a desired direction. Both slits 192 and 193 may be straight-cut slits. In some embodiments slits 192 and 193 maybe H-shaped as shown in FIG. 6. Alternatively, slits 192 and 193 may have a saw-tooth wave shape as shown in FIG. 7. Other suitable shaped slits are within the scope of the present invention.

In one preferred embodiment, as shown in FIG. 1A, the slit valve means 110 includes one elastomeric, thin diaphragm 195 that defines both the first and second slits 192 and 193. The elastomeric, thin diaphragm 195 is preferably made from silicone or other flexible materials. It is also contemplated that the diaphragm materials can be reinforced if desirable. For example, wires or fiber braids can be incorporated into the silicone or other flexible materials to reinforce the diaphragm 195. The shape of the diaphragm 195 and the shape of the valve housing 105 generally accommodate each other. Accordingly, suitable shapes for the diaphragm 195 include, but are not limited to, disc shape, rectangular shape, or overlapped double circle shape, or other suitable shapes.

In a preferred embodiment, the slit valve means 110 further includes slit valve securement means adjacent the periphery of the slit valve means. As illustrated in FIG. 1A, the slit valve securement means includes diaphragm securement members 197 and 199, each of which is disposed at one side of the diaphragm 195. Each diaphragm securement members 197 and 199 defines two apertures, each of which is centrally aligned with its corresponding slit on the diaphragm 195 so that the fluids can get across the slits. Diaphragm securement members 197 and 199 are preferably rigid, and can be formed of synthetic resinous materials. Under the assembled condition, as can be seen in FIG. 1A, the slit valve means 110 can be sandwiched between the female part 178 and the male part 182 of the valve housing 105. As a result, the diaphragm securement members 197 and 199 compressively support the elastomeric diaphragm 195 except to permit the first and second slits 192 and 193 on the diaphragm 195 to flex depending on pressure differential conditions associated with the first and second fluids, respectively.

Figure 2:
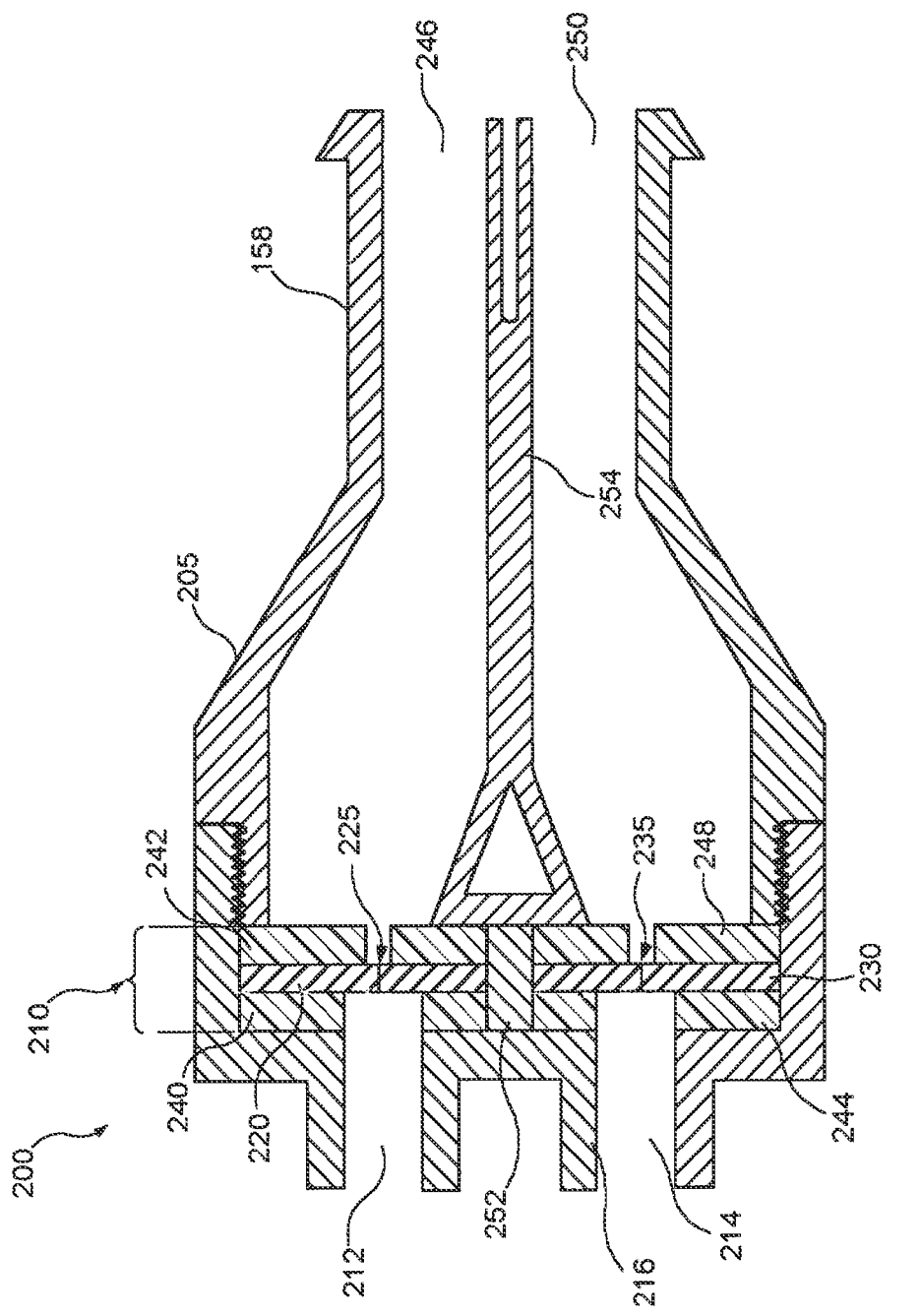
FIG. 2 is a schematic view of an alternative embodiment of a pressure responsive slit valve assembly of the present invention.

Another preferred exemplary embodiment of a pressure responsive slit valve assembly of the present invention is shown in FIG. 2. In this embodiment, the valve assembly 200 comprises a slit valve means 210 that includes two separate elastomeric, thin diaphragms, a first diaphragm 220 defining the first slit 225, and a second diaphragm 230 defining the second slit 235. Both first and second diaphragms 220 and 230 are preferably made from silicone or other flexible materials. It is also contemplated that the diaphragm materials can be reinforced if desirable. For example, wires or fiber braids can be incorporated into the silicone or other flexible materials to reinforce the diaphragms 220 and 230. The first diaphragm 220 is disposed transversely between the first aperture 212 and the first conduit 246 such that the first slit 225 is responsive to a pressure differential associated with the first fluid. In particular, the first slit 225 remains in a closed position until a pressure differential having a predetermined force exists across the first slit 225. Once the pressure differential crosses over this predetermined force threshold, the first slit 225 deforms, thereby allowing the first fluid to flow therethrough in a desired direction. Likewise, the second diaphragm 230 is disposed transversely between the second aperture 214 and the second conduit 250 such that the second slit 235 is responsive to a pressure differential associated with the second fluid. In particular, the second slit 235 remains in a closed position until a pressure differential having a predetermined force exists across the second slit 235. Once the pressure differential crosses over this predetermined force threshold, the second slit 235 deforms, thereby allowing the second fluid to flow therethrough in a desired direction. Both slits 225 and 235 may be straight-cut slits, H-shaped slits, saw-tooth wave shaped slits, or other suitable shaped slits.

The shapes of the first and second diaphragms 220 and 230 and the shape of the valve housing 205 generally accommodate one another. Accordingly, suitable shapes for the first and second diaphragms 220 and 230 include, but are not limited to, disc shape, rectangular shape, or other suitable shapes.

In a preferred embodiment, the slit valve means 210 further comprises slit valve securement means adjacent the periphery of the slit valve means. As illustrated in FIG. 2, the slit valve securement means includes diaphragm securement members 240 and 242 disposed at each side of the first diaphragm 220, and diaphragm securement members 244 and 248 disposed at each side of the second diaphragm 230. Each diaphragm securement members 240 and 242 defines one aperture that is centrally aligned with the first slit 225 so that the first fluid can get across the first slit 225. Similarly, each diaphragm securement member 244 and 248 defines one aperture that is centrally aligned with the second slit 235 so that the second fluid can get across the second slit 235. All of the diaphragm securement members 240, 242, 244, and 248 are preferably rigid, and can be formed of synthetic resinous materials.

It can be readily appreciated by one of skill in the art that the valve housing 205 can be modified in many different ways to accommodate the configuration of two separated diaphragms. For example, as illustrated in FIG. 2, the valve housing 205 can further include an additional wall 252 to separate, as well as to support the first and second diaphragms 220 and 230. The wall 252 can perpendicularly join to the interior surface of the vertical wall 216. Alternatively, the wall 252 can integrally join the internal walls 254 in the valve housing 205. Accordingly, under the assembled condition, as can be seen in FIG. 2, the diaphragm securement members 240 and 242 compressively support the first elastomeric diaphragm 220 while permit the first slit 225 to flex depending on pressure differential conditions associated with the first fluid. Likewise, the diaphragm securement members 244 and 248 compressively support the second elastomeric diaphragm 230 while permit the second slit 235 to flex depending on pressure differential conditions associated with the second fluid.

Although the slit valve means illustrated in either FIG. 1A or FIG. 2 is disposed adjacent to the first and second apertures, it is contemplated that a slit valve means may be disposed transversely anywhere between the first and second apertures and the first and second conduits. In the embodiments that a slit valve means is not disposed adjacent to the apertures, it is within the skill of an ordinary artisan in the field to modify the valve housing accordingly to accommodate the placement of the slit valve means.

It is further contemplated that a pressure responsive slit valve assembly of the present invention can be incorporated into multi-lumen or dual-lumen PICC catheters, multi-lumen or dual-lumen tunneled central venous catheters, and multi-lumen or dual-lumen dialysis catheters. For example, instead of placing individual valves in the external extension tubes, a dual-lumen valve assembly of the present invention can be incorporated into the currently-used V-connector in a dual-lumen PICC catheter. Further more, incorporation of the present invention permits a proximally trimmable PICC catheter. It is within the skill of an ordinary artisan to modify the scale, the dimension and the material of a pressure responsive slit valve assembly to accommodate the configuration of a multi-lumen or dual-lumen catheter. By way of example and not limiting, a perspective view of an exemplary embodiment of a pressure responsive slit valve assembly adapted for use with a PICC catheter is shown in FIG. 8A, a schematic view of an exemplary embodiment of a pressure responsive slit valve assembly adapted for use with a PICC catheter is shown in FIG. 8B, and a schematic view of an exemplary embodiment of a pressure responsive slit valve assembly with a dual-lumen PICC catheter attached thereon is shown in FIG. 8C. As depicted in FIGS. 8A, 8B, and 8e, the valve assembly optionally comprises suture wings with suture holes thereon, and barbs or lure threads on the exterior surfaces of connection ports and extrusion stems. It can be readily appreciated by one of skill in the art that the numbers and the configurations of the suture wings, suture holes, barbs and lure threads can be modified in many different ways to accommodate a desired configuration of a catheter.

Figure 9:
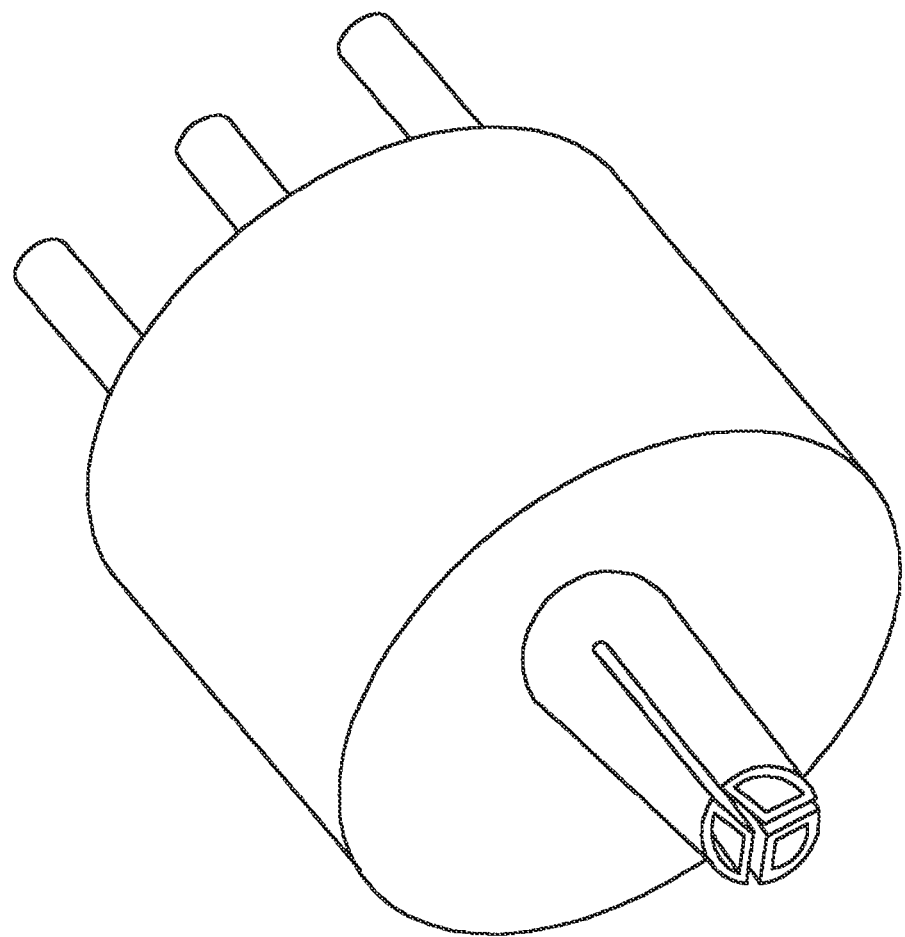
FIG. 9 is a perspective view of an exemplary embodiment of a triple-cavity pressure responsive slit valve assembly of the present invention.

It is further contemplated that a pressure responsive slit valve assembly of the present invention can be configured to communicate with more than two fluid sources. Accordingly, a valve housing can be further adapted to receive one additional fluid from an additional source. For example, the valve housing can define at least one additional aperture and at least one additional corresponding conduit. Likewise, the slit valve means can also include at least one additional pressure responsive slit corresponding with the additional fluid source. By way of example and not limiting, a perspective view of a triple-cavity pressure responsive slit valve assembly is shown in FIG. 9.

Figure 10:
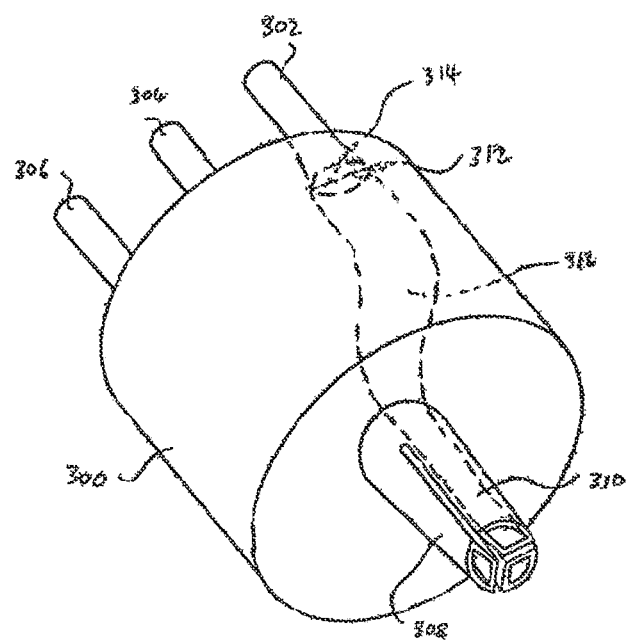
FIG. 10 is a schematic view showing internal passages of the valve assembly shown in FIG. 9.

One exemplary embodiment of the triple cavity pressure responsive slit valve is shown in FIG. 10. A triple cavity slit valve assembly 300 is shown in a perspective view with selected internal passages shown in dashed lines. In this embodiment, three apertures 302, 304, 306 at one end of the valve assembly 300 correspond to three conduits on the opposite end. Specifically, one of the additional corresponding apertures 302 is connected by a flow passage 316 of the valve assembly 300 to a corresponding additional conduit 310 of the extrusion stem 308. Within the flow passage 316 of the additional conduit 310 there is located an additional slitted membrane 314 with an additional pressure responsive slit 312. The operation of the triple cavity valve assembly 300 is analogous to the operation of the valves according to the invention described above.

It is further contemplated that the present invention provides a kit for adapting a medical device to accommodate a plurality of fluids. In a preferred embodiment, a kit of the present invention typically includes a pressure responsive slit valve assembly that is adapted for connecting to a desired medical device to receive fluids from at least two sources. The assembly typically comprises a slit valve means corresponding to each fluid source. In another preferred embodiment, a kit of the present invention may further include securement means for securely adapting the pressure responsive slit valve assembly to a desired medical device.

Variations, modifications, and other implementations of what is described herein will occur to those of ordinary skill in the art without departing from the spirit and scope of the invention. The invention is not to be limited only to the preceding illustrative description.

What is claimed is:

1. A medical catheter comprising:
    a valve housing comprising a first and second proximal valve housing opening and a first and second distal valve housing opening, a medical catheter comprising a first and second proximal catheter opening and a first and second distal catheter opening, a distal end of the valve housing being coupled to a proximal end of the medical catheter, the valve housing further comprising:
        first and second flow paths, wherein the first flow path establishes fluid communication between the first proximal valve housing opening, the first distal valve housing opening, the first proximal catheter opening, and the first distal catheter opening, and wherein the second flow path establishes fluid communication between the second proximal valve housing opening, the second distal valve housing opening, the second proximal catheter opening, and the second distal catheter opening;
    an internal wall preventing fluid communication between the first and second flow paths; and
    an elastomeric diaphragm comprising first and second slit valves formed therein, the first and second slit valves each having a proximal and a distal facing surface, wherein the first slit valve is disposed across the first flow path with proximal and distal facing surfaces in fluid communication with the first flow path, and the second slit valve is disposed across the second flow path with proximal and distal facing surfaces in fluid communication with the second flow path, the first slit valve opening in response to a first predetermined fluid pressure differential applied thereto, and the second slit valve opening in response to a second predetermined fluid pressure differential applied thereto.

2. The medical catheter of claim 1, wherein the elastomeric diaphragm is substantially planar.

3. The medical catheter of claim 1, further comprising slit valve securement means, wherein the elastomeric diaphragm is disposed transversely to and compressed by said slit valve securement means.

4. The medical catheter of claim 1, further comprising male and female housing portions securably engaged with one-another, wherein the elastomeric diaphragm is disposed between said male and female housing portions and compressed therebetween.

5. The medical catheter of claim 1, wherein the elastomeric diaphragm is reinforced with one of a wire and a fiber braid.

6. The medical catheter of claim 1, further comprising:
    an outlet insertable into a multi-lumen catheter, the outlet including a recess sized to accommodate an inner wall of the multi-lumen catheter.

* * * * *